US010588737B2

(12) United States Patent
McClellan (10) Patent No.: US 10,588,737 B2
(45) Date of Patent: Mar. 17, 2020

(54) TISSUE EXPANDER IMPROVEMENTS (71) Applicant: William T. McClellan, Morgantown, WV (US)

(72) Inventor: William T. McClellan, Morgantown, WV (US)

(*) Notice: Subject to any disclaimer, the term of this patent is extended or adjusted under 35 U.S.C. 154(b) by 0 days.

(21) Appl. No.: 16/016,865

(22) Filed: Jun. 25, 2018

(65) Prior Publication Data

US 2018/0303600 A1 Oct. 25, 2018

Related U.S. Application Data

(63) Continuation of application No. 15/029,816, filed as application No. PCT/US2014/061075 on Oct. 17, 2014, now Pat. No. 10,010,404.

(60) Provisional application No. 61/892,847, filed on Oct. 18, 2013.

(51) Int. Cl.
*A61F 2/12* (2006.01)
*A61B 90/00* (2016.01)

(52) U.S. Cl.
CPC ............... *A61F 2/12* (2013.01); *A61B 90/02* (2016.02); *A61F 2250/0002* (2013.01); *A61F 2250/0013* (2013.01); *A61F 2250/0087* (2013.01)

(58) Field of Classification Search
CPC .......... A61F 2/12; A61F 128/898; A61B 5/06
USPC ....................................................... 623/7–8
See application file for complete search history.

(56) References Cited

U.S. PATENT DOCUMENTS

| | | | |
|---|---|---|---|
| 4,671,255 A | 6/1987 | Dubrul et al. |
| 5,630,843 A | 5/1997 | Rosenberg |
| 5,944,023 A | 8/1999 | Johnson et al. |
| 6,044,297 A | 3/2000 | Sheldon et al. |
| 7,736,391 B2 | 6/2010 | Schwibner et al. |
| 7,871,438 B2 | 1/2011 | Corbitt |
| 8,015,977 B2 | 9/2011 | Bertrand et al. |
| 8,387,817 B1 | 3/2013 | Zelechonok |

(Continued)

FOREIGN PATENT DOCUMENTS

| | | |
|---|---|---|
| WO | 2011/063349 | 5/2011 |
| WO | 2011/075731 | 6/2011 |
| WO | 2018078446 A1 | 3/2018 |

OTHER PUBLICATIONS

International Search Report for PCT/US2014/061075 dated Jan. 29, 2015, 2 pages.

(Continued)

*Primary Examiner* — Suzette J Gherbi
(74) *Attorney, Agent, or Firm* — Andrew D. Wright; Roberts Calderon Safran & Cole P.C.

(57) ABSTRACT

Improvements for use with tissue expanders are provided. A first aspect includes a tissue expander device provided with a colorant inside a shell before the shell is inflated with fluid, wherein the colorant mixes with fluid upon injection of fluid into the shell. A second aspect includes a tissue expander device provided with a tread on an exterior surface of the shell. A third aspect includes a system having: a computing device with a visual display screen; a detector connected to the computing device that is configured to detect a port of a tissue expander that is implanted under skin of a patient; and software running on the computing device that receives signals from the detector and causes the visual display screen to show a visual representation of a location of the detected port of the tissue expander.

20 Claims, 5 Drawing Sheets

(56) References Cited

U.S. PATENT DOCUMENTS

| | | | |
|---|---|---|---|
| 8,454,690 B2* | 6/2013 | McClellan | A61B 90/02 |
| | | | 604/103.02 |
| 9,144,488 B2* | 9/2015 | Boyden | A61F 2/12 |
| 9,268,915 B2* | 2/2016 | Holmes | G06F 19/3418 |
| 9,333,071 B2* | 5/2016 | Boyden | G01N 33/528 |
| 9,814,566 B1 | 11/2017 | Cree | |
| 10,010,404 B2* | 7/2018 | McClellan | A61F 2/12 |
| 10,252,145 B2* | 4/2019 | Tran | H04N 5/2257 |
| 2005/0061198 A1 | 3/2005 | Khan et al. | |
| 2007/0288095 A1 | 12/2007 | Wirtel et al. | |
| 2008/0033471 A1 | 2/2008 | Paz et al. | |
| 2008/0091175 A1 | 4/2008 | Frikart et al. | |
| 2008/0161929 A1 | 7/2008 | McCormack et al. | |
| 2009/0012372 A1* | 1/2009 | Burnett | A61B 5/076 |
| | | | 600/300 |
| 2009/0157180 A1 | 6/2009 | Schraga | |
| 2010/0256775 A1 | 10/2010 | Belhe et al. | |
| 2011/0153017 A1* | 6/2011 | McClellan | A61F 2/12 |
| | | | 623/8 |
| 2011/0208311 A1 | 8/2011 | Janowski | |
| 2012/0041305 A1 | 2/2012 | Grissom et al. | |
| 2012/0184893 A1 | 7/2012 | Thompson et al. | |
| 2012/0302874 A1* | 11/2012 | Hollstien | A61B 5/0084 |
| | | | 600/424 |
| 2013/0190796 A1 | 7/2013 | Tilson et al. | |
| 2013/0325120 A1* | 12/2013 | McClellan | A61F 2/12 |
| | | | 623/8 |
| 2013/0338769 A1* | 12/2013 | Boyden | A61F 2/12 |
| | | | 623/8 |
| 2014/0121771 A1 | 5/2014 | Chitre et al. | |
| 2016/0066979 A1 | 3/2016 | Mueller et al. | |
| 2016/0250017 A1 | 9/2016 | McClellan | |
| 2016/0310306 A1 | 10/2016 | Brister et al. | |
| 2017/0228627 A1 | 8/2017 | Geissler et al. | |
| 2017/0246019 A1 | 8/2017 | Miesse et al. | |

OTHER PUBLICATIONS

Written Opinion of the International Search Authority for PCT/US2014/061075 dated Jan. 29, 2015, 5 pages.

Notification Concerning Transmittal of International Preliminary Report on Patentability for PCT/US2014/061075 dated Apr. 28, 2016, 1 page.

Preliminary Report on Patentability for PCT/US2014/061075 dated Apr. 19, 2016, 1 page.

International Search Report and Written Opinion issued in a application PCT/US19/17269 dated May 1, 2019, 8 pages.

* cited by examiner

TISSUE EXPANDER IMPROVEMENTS

CROSS REFERENCE

This application is a Continuation of U.S. patent application Ser. No. 15/029,816 filed on Apr. 15, 2016, which is a National Stage entry of International Application No. PCT/US2014/061075 filed on Oct. 17, 2014, which claims priority to U.S. Provisional Patent Application No. 61/892,847, filed Oct. 18, 2013, the contents of which are incorporated by reference in their entirety.

FIELD OF THE INVENTION

The invention generally relates to medical devices and associated methods of manufacture and use, and more particularly to tissue expanders.

BACKGROUND

Breast reconstruction with a tissue expander (TE) is currently the most common technique used for breast reconstruction. Typically immediately after the female has a mastectomy the reconstructive medical professional places a tissue expander which serves to stretch the skin and muscle in order to make room for a future implant or maintain the existing skin envelope. Prosthetic reconstruction of the breast, as a staged procedure with tissue expanders followed by implants, is a reliable method for breast reconstruction that offers favorable aesthetic and psychological results while adding only minimal additional surgical intervention. Today, the process usually involves the placement of a tissue expander under the pectoralis major muscle and remaining skin of the absent breast. The tissue expander is then gradually inflated over several weeks or months by periodic injections of saline, causing the stretching and expansion of the overlying skin and muscle coverage. When adequate coverage is achieved, the tissue expander is typically removed, and a permanent breast implant is placed into the expanded space.

SUMMARY

In a first aspect of the invention, there is a tissue expander device comprising: a selectively inflatable and deflatable shell that is configured to be implanted; at least one port for selectively inflating and deflating the shell; and a colorant inside the shell before the shell is inflated with fluid, wherein the colorant mixes with the fluid upon injection of fluid into the shell. In embodiments, the colorant is dehydrated and the injecting the fluid into the shell to inflate the body rehydrates the colorant. In embodiments, upon mixing with the injection fluid, the colorant turns the clear injection fluid to another non-clear color. In embodiments, a wafer or sticker or tab of the colorant is placed on an underside of the at least one port, or on an inside surface of the interior wall of the shell. In embodiments, the colorant is biocompatible. Aspects of the invention also include a method of manufacturing the tissue expander device. Aspects of the invention also include a method of using the tissue expander device.

In another aspect of the invention, there is a tissue expander device comprising: a selectively inflatable and deflatable shell that is configured to be implanted; at least one port for selectively inflating and deflating the shell; a tread on an exterior surface of the shell. In embodiments, the tread is on a back side of the shell. In embodiments, the tread comprises a first area and a second area, the first area has a plurality of treads in a first direction, and the second area has a plurality of treads in a second direction different than the first direction. In embodiments, the tread comprises a third area and a fourth area, the third area has a plurality of treads in a third direction, the fourth area has a plurality of treads in a fourth direction, and the first, second, third, and fourth directions are all different from one another. In embodiments, the tread is one of adhesively attached to the shell, welded to the shell, and molded with the shell. In embodiments, the tread covers the entire back surface of the shell. In other embodiments, the tread covers discrete spots on the back surface of the shell. Aspects of the invention also include a method of manufacturing the tissue expander device. Aspects of the invention also include a method of using the tissue expander device.

In another aspect of the invention, there is a tissue expander device comprising: a selectively inflatable and deflatable shell that is configured to be implanted; at least one port for selectively inflating and deflating the shell; a tread on an exterior surface of the shell; and a colorant inside the shell before the shell is inflated with fluid, wherein the colorant mixes with the fluid upon injection of fluid into the shell. Aspects of the invention also include a method of manufacturing the tissue expander device. Aspects of the invention also include a method of using the tissue expander device.

In another aspect of the invention, there is a system comprising: a computing device with a visual display screen; a detector connected to the computing device that is configured to detect a port of a tissue expander that is implanted under skin of a patient; and software running on the computing device that receives signals from the detector and causes the visual display screen to show a visual representation of a location of the detected port of the tissue expander. In embodiments, the detector and software are configured to change the display based on changing at least one of the location and orientation of the detector relative to the port. In embodiments, the detector and software are configured to change the display based on at least one of translating, rolling, pitching, and yawing the detector relative to the port. In embodiments, the detector and software are configured to change the display to show visual indicator when the detector is located and oriented in a correct position relative to the port. In embodiments, the computing device is a smartphone and the software is an app running on the smartphone.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
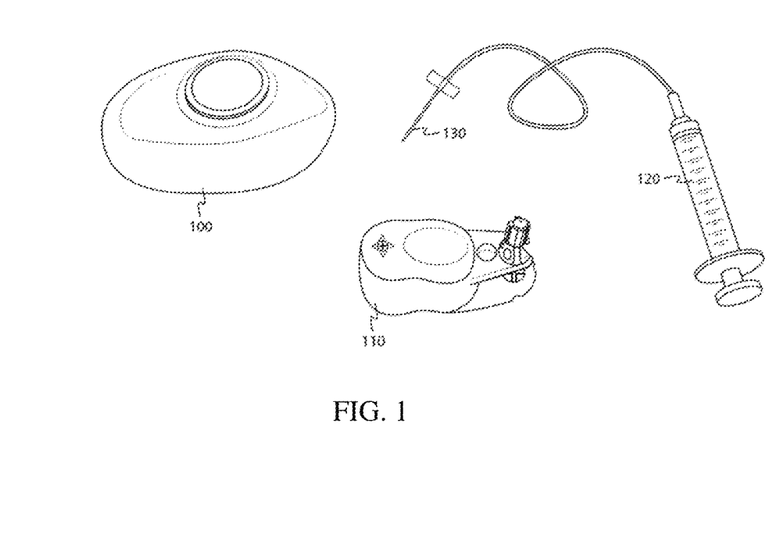
FIG. 1 shows a system used for tissue expansion, which may include a tissue expander, a magnet, and a fluid delivery system.

FIG. 1 shows a system used for tissue expansion, which may include a tissue expander 100, a magnet 110, and a fluid delivery system 120. The magnet 110 may be used to detect a particular portion of the tissue expander 100, such as an access port 140 (also called an implant port). The fluid delivery system 120 may include a needle 130 or other end used to access the interior of the tissue expander 100. The fluid delivery system 120 may provide a fluid to the interior (e.g., internal cavity defined by an implant shell 115) of the tissue expander 100 to cause the tissue expander 100 to expand. In some embodiments, the fluid delivery system 120 may also be used to access the interior of the tissue expander 100 to remove fluid from the tissue expander 100, which may cause the tissue expander 100 to contract or deflate.

Figure 2:
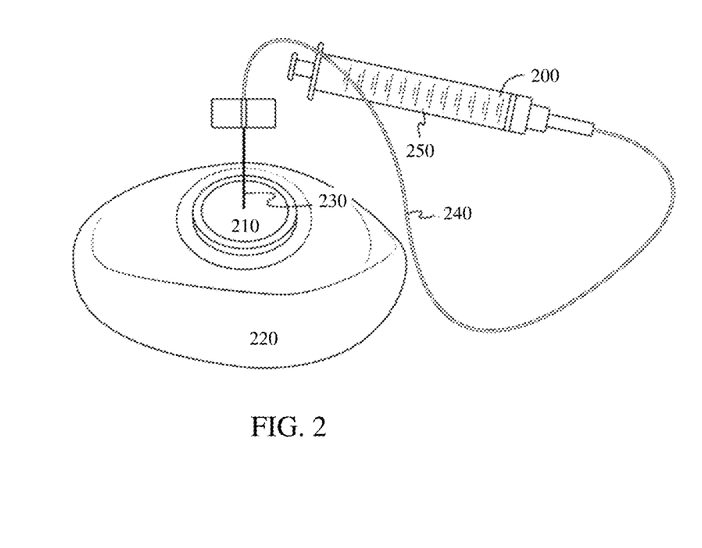
FIG. 2 shows an example of a fluid delivery system providing access to an access port of a tissue expander.

FIG. 2 shows an example of a fluid delivery system 200 providing access to an access port 210 of a tissue expander 220 comprising an implant shell 215. The fluid delivery system 200 may include a needle 230 and a tube 240 to provide fluid to the interior of the tissue expander 220 via the access port 210 (e.g., inflation/deflation port). The needle may puncture the access port 210 to provide fluid to, or remove fluid from, the interior (e.g., internal cavity) of the tissue expander. The access port 210 may be provided with a self-healing/sealing material that, after being punctured by a needle of the fluid delivery system 200, reforms an airtight and liquid tight seal. In some instances, the fluid delivery system 200 may utilize a tip other than a needle that may be capable of delivering a fluid to, and removing fluid from, the tissue expander 220.

A pressure differential may be created to cause fluid to flow into or out of the tissue expander 220. For example, a positive pressure may be provided from outside the tissue expander 220, which positive pressure causes inflation of the tissue expander 220. In one example, a syringe 250 may be used to provide the positive pressure. In another example, a negative pressure may be provided from within the tissue expander 220 to draw fluid out of the tissue expander 220 for deflation of the tissue expander 220. Alternatively, pumps or valves may be utilized to assist with fluid flow.

Figure 3:
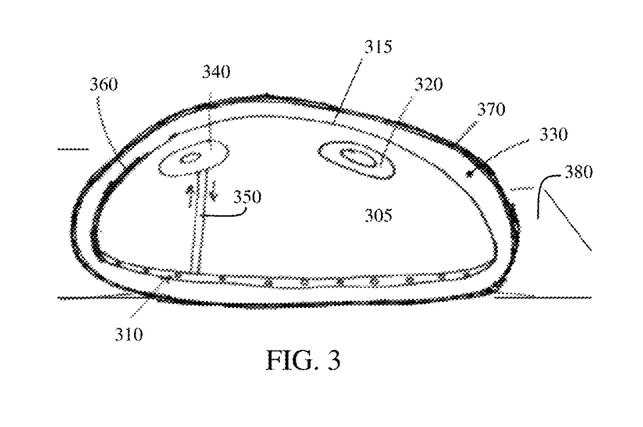
FIG. 3 provides an example of a tissue expander.

FIG. 3 provides an example of a tissue expander 300 in accordance with an embodiment of the invention. The tissue expander 300 may include an inside cavity 305 (e.g., internal cavity) and one or more channels 310 (also referred to herein as a delivery canal) around an implant shell 315. The inside cavity 305 may be defined by the implant shell 315. The implant shell 315 may be configured to contain a fluid within the inside cavity 305 in a fluid-tight manner, such that the tissue expander 300 may be inflated and deflated. The tissue expander 300 may include an implant port 320, which may be similar to access port 210 described herein. The implant port 320 may provide access to the inside cavity 305 of the implant and is where saline, water, air, or any other fluid, may be injected into or removed from the interior of the implant shell 315 for inflation and deflation of the tissue expander 300. Thus, an implant port 320 may provide fluidic access to the interior of the implant shell 315.

The implant shell 315 may have any shape and be composed of any suitable material in accordance with aspects of the invention. For example, the implant shell 315 may have a roughly spherical or hemispherical shape. Alternatively, the implant shell 315 may have an elongated shape. The implant shell 315 may also form various shapes that are suited for implanting into various locations of a subject's body. Such shapes may be designed to conform to a breast, scalp, face, neck, hands, arms, legs, or any other portion of a subject's body.

In embodiments, the one or more channels 310 about the implant shell 315 may provide a delivery/drainage system. Any discussion herein of a delivery/drainage system, channels, or canals may also apply to systems, channels, canals, or regions that may be used for delivery of a fluid and/or drainage/retrieval of a fluid. In embodiments, a delivery/drainage system may be connected to the implant shell 315. In some instances, the delivery/drainage system can be around the implant shell 315 or surround portions of the surface of the implant shell 315. The delivery/drainage system may leave at least a portion of the implant shell 315 exposed. Alternatively, the delivery/drainage system may substantially cover the entire exterior surface of the implant shell 315. The delivery/drainage system may be in fluidic communication with an exterior of the tissue expander 300 while not being in fluidic communication with the interior, e.g., inside cavity 305, of the implant shell 315 (i.e., the delivery system is fluidically isolated from the cavity defined within the implant shell).

As described herein, a pocket 330 is the space around a tissue expander 300 implant when the tissue expander 300 is implanted in a subject's body. The subject's body may form the pocket 330 as an area without blood vessels and, therefore, the pocket 330 may be isolated from antibiotics that are normally carried by the subject's vascular system.

In accordance with aspects of the invention, however, fluid communication with the pocket 330, or space or compartment around the tissue expander 300, may be provided via a percutaneous port such as a pocket port 340 and one or more channels 310 as described herein. In this manner, implementations of the invention may be used to deliver antibiotics, or any other fluids, to the pocket 330. Such communication may be provided for the drainage of any fluid within the pocket 330, or for the delivery of any fluid to the pocket 330. Devices in accordance with aspects of the invention may be adaptable to provide either or both of these functions.

The tissue expander 300 may also include a pocket port 340. In embodiments, the pocket port 340 may communicate with the channel(s) 310 around the implant shell 315. Thus, a pocket port 340 may provide fluidic access to a delivery/drainage system, which may include the channel(s) 310 and be in fluid communication with the pocket 330. The pocket port 340 can serve to deliver antibiotics or other fluids directly to the pocket 330 or it can be used to aspirate fluid from the pocket 330. In some instances, the pocket port 340 may be integral to the tissue expander 300, such as being formed integrally with the implant shell 315.

In some embodiments, at least one of the implant port 320 and pocket port 340 may comprise one or more remote ports. A remote port may be separate from the implant shell 315 portion of the tissue expander 300. For example, a separate area may be created surgically for a remote port to rest in or on the subject body. The remote port may be connected to the tissue expander 300 by a tubing system. In some embodiments, a tissue expansion system can have one or two remote ports fluidly connected to the inside cavity 305 of the shell 315 and/or to the channel system 310. The remote port can be disengaged (pulled out) when it is desirable to keep the tissue expander implanted in the patient for a long time and take out the port through a separate small incision.

An implant port 320 may be an integrated in the implant shell 315 of the tissue expander 300, or a remote port may be provided that provides the same function as the implant port 320. Similarly, a pocket port 340 may be integrated in the implant shell 315 of the tissue expander 300, or a remote port may be provided that provides the same function as the pocket port 340. Any number of additional ports may be provided which may be integral to the tissue expander or which may be provided as a remote port.

The tissue expander may have a channel system 310 (also called a channel or delivery canal) in accordance with embodiments of the invention. In some embodiments, the channel system 310 may include a french drain type tubing system that can be integral and tightly bound to the implant shell 315 of the tissue expander 300. The channel system 310 can be located anywhere and in any configuration on the implant shell 315 of the tissue expander 300. In some instances, the channel system 310 may be located anywhere on the tissue expander 300 implant. However, in some instances, it may be preferable to provide the channel system 310 on the posterior surface of the implant shell 315, with respect to the orientation of the tissue expander 300 within the subject's body, because when a subject lies in a supine position, the fluid may move dependently posterior due to gravity. In other instances, the channel system 310 may be provided on an anterior surface and/or along the sides of the implant shell 315.

In embodiments, the channel system 310 can be used to deliver antibiotics or other chemicals to a pocket 330 which forms around the tissue expander 300 (e.g., around the implant). The channel system 310 can also "suck up" fluid which lies around the implant to be sent for culture or just aspirate sterile fluid. The channel system 310 can have a variety of configurations. In some embodiments, the channel system 310 may have a relatively more rigid structure to it than the implant shell 315 because it may be desirable to prevent collapse of the channel system 310 under pressure of injection or aspiration.

In some embodiments, one or more communication channels 350 may be provided between the channel system 310 and a pocket port 340 (whether integral or remote). The communication channel 350 may be fluidically connected to both the channel system 310 and the pocket port 340 to enable fluid to flow to or from the channel system 310 from the pocket port 340.

As described in greater detail herein, one or more stability tabs may be provided to a tissue expander 300 in embodiments of the invention. The stability tab can either be sewn down or can be a solid structure extending like a training wheel from the implant shell and which may serve to prevent the implant from being turned over or accidentally flipping over during normal use.

A tissue expansion device may also have an outside covering 360 arranged on an outer surface of the implant shell 315. The outside covering 360 of the tissue expander 300 implant may be composed of an integral substance that dissolves over time and exposes the outer surface of the implant shell 315 over time. This may help prevent biofilms from persisting on the tissue expander 300. Biofilms are a community of bacteria which are very hard to treat. Bacteria exist on the surface of the implant and often establish these communities when the implant is initially placed, and there may be small colonies of bacterial contamination. In some embodiments, the outside covering 360 of the tissue expander 300 implant may be a bonded dissolvable material with or without antibiotics, silver, or another metal. The outside covering may still remain soft.

In embodiments, the outside covering 360 comprises a dissolving material, such as polydioxanone (PDS). The dissolving material of the outside covering 360 helps prevent the formation of biofilms on the exterior surface of the tissue expander 300. As the outside covering 360 dissolves, the material on which the biofilm is formed collapses, thereby helping eliminate the biofilm.

In accordance with aspects of the invention, a tissue expansion system such as tissue expander 300 may be provided within a capsule 370. As described herein, a capsule 370 is a fibrous shell that the subject's body forms around an implant placed in the body. The implant shell 315 and capsule 370 are separate entities and there is a potential space, such as pocket 330, between them. The capsule 370 has very limited blood supply and usually has a smooth tough surface. The capsule 370 may form a physical barrier from the subject's body, vascular system, and immune system, and may serve as the boundary of a pocket 330.

In some embodiments, a tissue expander 300 may be positioned adjacent to, or in the proximity of, a firm area 380 such as, for example, a chest wall, skull, or any other bodily support structure or firm area from which to expand skin. In some embodiments, a posterior side of the tissue expander 300 may be the side of the tissue expander 300 located more closely to the firm area 380. An anterior side of the tissue expander 300 may be the side of the tissue expander located opposite the posterior side, and away from the firm area 380. In some instances, a tissue expander 300 is not positioned adjacent to a firm area 380. In such situations, the anterior side of the tissue expander 300 may be the side that is closer to the skin of the subject, while the posterior side may be the side deeper within the subject.

Thus, in accordance with aspects of the invention and as described herein, a tissue expander 300 may comprise an implant shell 315, an internal cavity 305 defined by an interior of the implant shell 315, and a channel 310 on an exterior portion of the implant shell 315. An access port 320 (also called an access port) provides selective fluid communication with the cavity 305 such that the implant shell 315 may be inflated (or deflated) by introducing fluid into (or extracting fluid out of) the cavity 305. The tissue expander 300 may further comprise at least one channel 310 arranged on an exterior portion of the implant shell 315. A pocket port 340 provides selective fluid communication with the channel 310 via a communication channel 350. In embodiments, the channel 310 has a plurality of holes (e.g., apertures, bores, slits, etc.) that provide fluid communication between an interior of the channel 310 and an exterior of the channel 310. In this manner, the pocket port 340, communication channel 350, and channel 310 provide a system for selectively introducing fluid to (or extracting fluid from) the pocket 330 around the exterior of the implant shell 315 in the patient's body. In embodiments, the access port 320 does not communicate with the channel 310, and the pocket port 340 does not communicate with the cavity 305. As such, in embodiments, the access port 320 and pocket port 340 comprise mutually exclusive ports for: (i) selectively controlling the inflation/deflation of the tissue expander 300 and (ii) injecting/extracting fluid to/from the pocket 330, respectively.

In accordance with an aspect of the invention, a tissue expander may include one or more inside cavities defined by a tissue expander shell and a surrounding channel system. The tissue expander may be incorporate features, components, or characteristics of other implants such as those described in: U.S. Pat. Nos. 5,330,843; 4,800,901; U.S. Patent Publication No. 2007/0233273; U.S. Pat. Nos. 6,666,893; 6,206,930; 7,575,597; and 8,454,690, the disclosures of all of which are incorporated by reference herein in their entirety.

Figure 4:
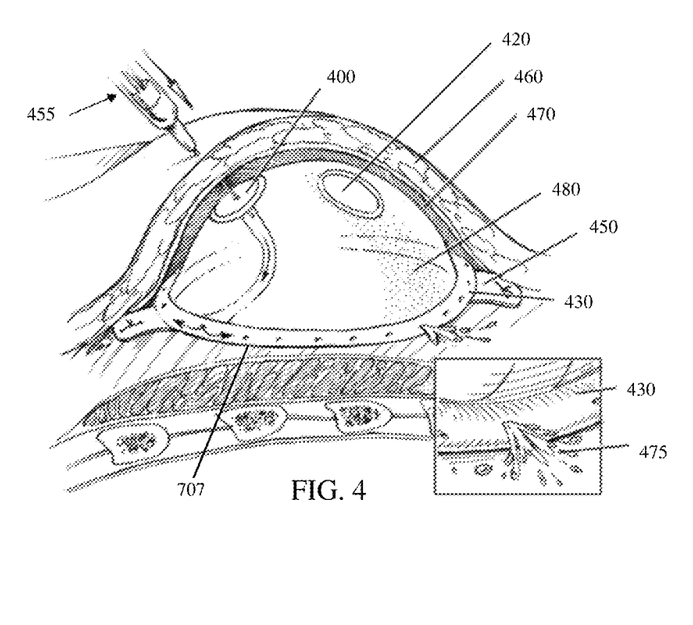
FIG. 4 shows an additional view of a tissue expander with integrated ports.

FIG. 4 shows an additional view of a tissue expander that may be used in aspects described herein implanted in a patient. In embodiments, the tissue expander includes an implant shell 415 provided with an integrated pocket port 400 and an integrated access port 420 (also called an implant port). The access port 420 may be configured to permit the introduction of fluid into the interior of the shell 415 for inflating the tissue expander. The pocket port 400 may be fluidically connected to a channel system comprising the delivery canal 430 having multiple openings. Fluid may be provided via needle 455 through the pocket port 400 to the delivery canal 430 and out to the area surrounding the tissue expander, e.g., the pocket. In some embodiments, the fluid may be an antibiotic solution.

The tissue expander may be provided under the skin and/or subcutaneous tissue 460 of a subject. A pocket 470 may be provided as the potential space between the tissue expander and the capsule, or tissue surrounding the tissue expander. When fluid 475 is delivered through the delivery canal 430, it may be delivered to the pocket surrounding the tissue expander.

One or more stability tabs 450 may be provided on the tissue expander. In some embodiments, the stability tabs 450 may protrude from beneath the delivery canal 430.

The tissue expander may have an antibiotic and/or antimicrobial coating 480. In some embodiments, the tissue expander may have a dissolvable cover such as PDS or Monocryl. The dissolvable cover, which may or may not be used in combination with an antibiotic or antimicrobial coating, may prevent or delay the establishment of a biofilm. As the dissolvable cover dissolves away, bacteria loses the ability to attach to the tissue expander, thereby inhibiting the growth of the biofilm.

Colorant

Figure 5:
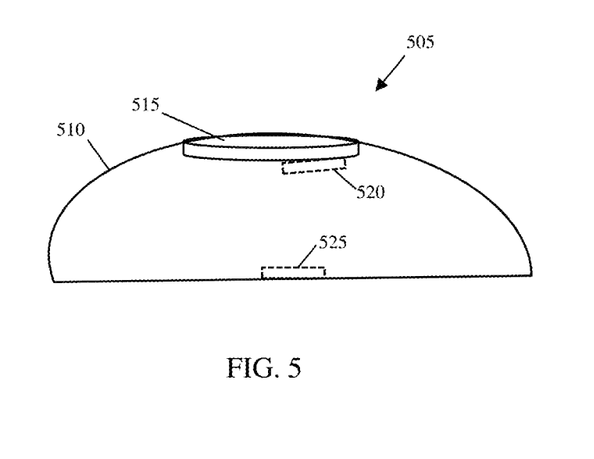
FIGS. 5 and 6 show aspects of a tissue expander with colorant in accordance with aspects of the invention.
Figure 6:
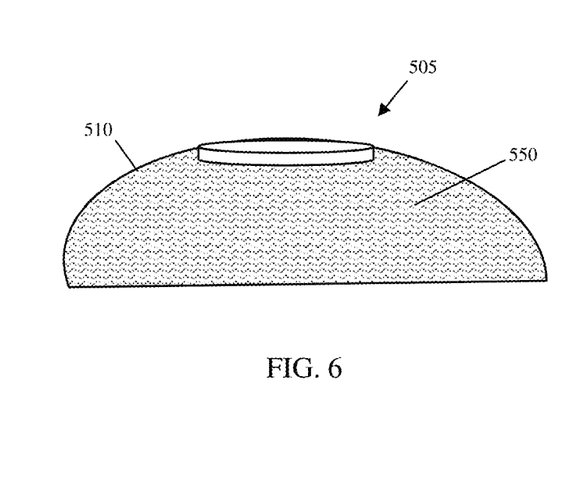

FIGS. 5 and 6 show aspects of a tissue expander with colorant in accordance with aspects of the invention. During a skin sparing mastectomy and/or tissue expander reconstruction, the medical professional inflates (expands) a tissue expander by injecting saline into the interior of the shell of the tissue expander. It is common to inadvertently injure (e.g., puncture) the shell of the tissue expander with a suture needle while the medical professional (e.g., surgeon) is closing the muscle, allograft, dermis, or skin around the tissue expander. When a medical professional accidentally sticks the tissue expander with a needle, the tissue expander does not pop but rather slowly drains a small amount of the saline contained inside the tissue expander shell. Because the saline is clear (e.g., colorless), the medical professional may not notice the leaking fluid since the wound is moist and bloody, and also because the leaking saline may visually blend in with clear irrigation fluid that is applied to the wound.

To address this problem, implementations described herein provide a technical solution to this problem by adding a colorant to the saline that is used to inflate the tissue expander. The colorant causes the saline to have a color, rather than being clear. In this manner, when the tissue expander is accidentally punctured, the leaking fluid is readily noticeable due to its color, and the medical professional is prompted to take corrective action regarding the puncture. Although this description uses saline as an illustrative example, it is to be understood that implementations are not limited to use with saline, and aspects of this embodiment may be practiced with any clear fluid that is used to fill (e.g., inflate) a tissue expander.

In one embodiment, the colorant is added to the saline prior to the saline being introduced into the tissue expander. For example, a small amount of methylene blue is added to a bag of saline before the saline from the bag is placed into the tissue expander to inflate the tissue expander. In this manner, the saline is blue as it is being added to the interior of the tissue expander. In the event that the tissue expander is accidentally punctured (e.g., stuck by a needle, manufacturing defect, etc.), the blue saline leaks from the inside of the tissue expander to outside the tissue expander and is noticeable by the medical professional (e.g., alerts the medical professional to the puncture).

In other implementations, the colorant is placed in the tissue expander before the tissue expander is inflated with fluid. For example, a dry (dehydrated, powdered, etc.) form of the colorant may be placed inside the interior of a dry tissue expander. When the medical professional injects clear fluid (e.g., saline) into the tissue expander to inflate the TW, the fluid rehydrates the colorant, and causes the fluid to change color (e.g., blue). If the tissue expander is punctured, the blue fluid inside the tissue expander leaks out around the area of the puncture and alerts the medical professional to the puncture. This embodiment has a benefit that the colorant can be added at the time of manufacture of the tissue expander, rather than the medical professional having to add the colorant. Also, by adding the colorant at the time of manufacture, the sterility of the tissue expander may be maintained.

In embodiments, the dehydrated colorant may be placed in many suitable locations inside the tissue expander, as illustrated in FIG. 5. For example, a wafer or sticker or tab of the colorant may be placed on an underside of the tissue expander fill port (such as access port 140, 210, 320 or 420), or on an inside surface of the interior wall of the tissue expander (e.g., on an interior surface of implant shell 115, 215, 315, or 415). In all cases, the colorant used may be minimal and biocompatible. For example, the colorant may comprise methylene blue that is initially in a dry and solid state inside the tissue expander prior to the saline being added to the interior of the tissue expander, and that dissolves in the saline and turns the saline blue when the saline is introduced inside the tissue expander. In a preferred embodiment, the dry colorant is in the form of a wafer, sticker, or tab, rather than a loose powder. This is because a tissue expander is packaged in a sterilized manner with air inside the tissue expander, and the medical professional removes the air from the interior of the tissue expander prior to implanting the tissue expander in the patient body. A powdered colorant may disadvantageously be sucked out of the tissue expander when removing the air, but a wafer, sticker, or tab will remain inside the tissue expander during the air removal. However, aspects of the invention are not limited to a wafer, sticker, or tab; instead any suitable colorant may be used, including powder, liquid, dehydrated powder, etc.

In further embodiments, the colorant may be temperature activated. For example, the colorant may not be active at room temperature, and may be activated when warm saline comes into contact with the colorant.

FIG. 5 shows an example of a tissue expander 505 with a colorant in accordance with aspects of the invention. The tissue expander 505 includes a shell 510 and an access port 515, which may the same as or similar to one of the shells and access ports described with respect to FIGS. 1-4. The tissue expander 505 may include a colorant on an interior surface of the shell 510, as indicated by reference number 520. Additionally or alternatively, the tissue expander 505 may include the colorant on an interior surface of the access port 515, as indicated by reference number 525. In embodiments, the colorant is a dry and solid substance that dissolves in saline and yields a colored solution when the saline is introduced to the interior of the shell 510. In a particular embodiment, the colorant is a wafer, sticker, or tab of methylene blue, as described herein. In FIG. 5, the tissue expander 505 contains only air inside the shell 510, and does not yet contain any saline. FIG. 6 shows the tissue expander 505 after saline has been injected into the shell 510 via the access port 515. The colorant (shown in FIG. 5) is dissolved in the saline 550 and causes the saline 550 to have a visible color (e.g., blue).

Any one or more of the colorant aspects described with respect to FIGS. 5-6 may be used with any type of tissue expander, including but not limited to any of the tissue expanders depicted in FIGS. 1-4. Any one or more of the various colorant aspects described with respect to FIGS. 5-6 may be used alone or with the tread described with respect to FIGS. 7-11 and/or the locator described with respect to FIGS. 12-14.

Tread

FIGS. 7-11 show aspects of a tissue expander tread in accordance with aspects of the invention. Conventional tissue expanders suffer from the problem that the implanted tissue expander can turn, spin, or dislodge from its initial position within the patient body. Such movement may result in an unwanted position of the tissue expander within the body (such as the tissue expander flipping within the body), or potential damage to the tissue expander which can require replacing the tissue expander.

A tissue expander may be sutured to the patient body to prevent movement of the tissue expander within the patient body. For example, as shown in FIG. 4, the tissue expander may include tabs that are configured to be sutured to a portion of the patient body (e.g., the chest wall). Sutures can be disadvantageous, however, when later removing an implanted tissue expander since the medical professional must locate and cut the suture to release the tissue expander from the patient body.

Figure 7:
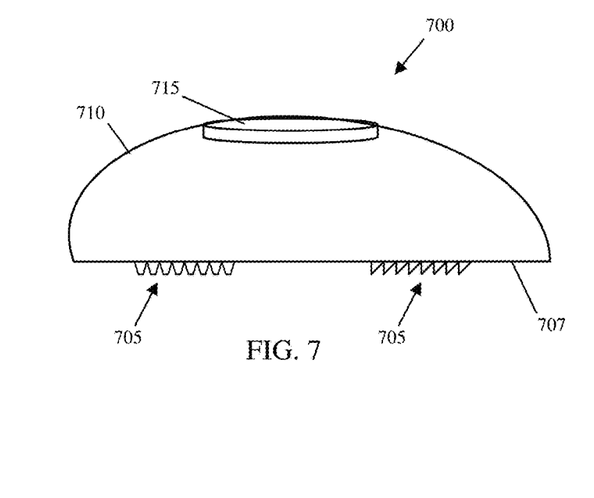
FIGS. 7-11 show aspects of a tissue expander tread in accordance with aspects of the invention.

To address this problem, implementations described herein provide a technical solution to this problem by providing a tread or gripping pattern that is provided on the exterior of a tissue expander (tissue expander) to prevent movement and slippage of the tissue expander within the patient body when the tissue expander is implanted in the body. For example, FIG. 7 shows a tissue expander 700 including a shell 710 and an access port 715, which may the same as or similar to one of the shells and access ports described with respect to FIGS. 1-4. In embodiment, the tissue expander 700 includes treads 705 formed on an outer surface 707 of the shell 710 in accordance with aspects of the invention. In embodiments, the outer surface 707 is a backside (or underside) of the shell that is configured to lay against the chest wall of the patient when the tissue expander is implanted in the patient, as depicted in FIG. 4. The treads 705 may be ridges or material similar in pattern to the tread of a running shoe or hiking boot. The ridges may be divided into sections that are spaced in different configurations and/or patterns. The ridges may have rounded or sharp edges.

Figure 8:
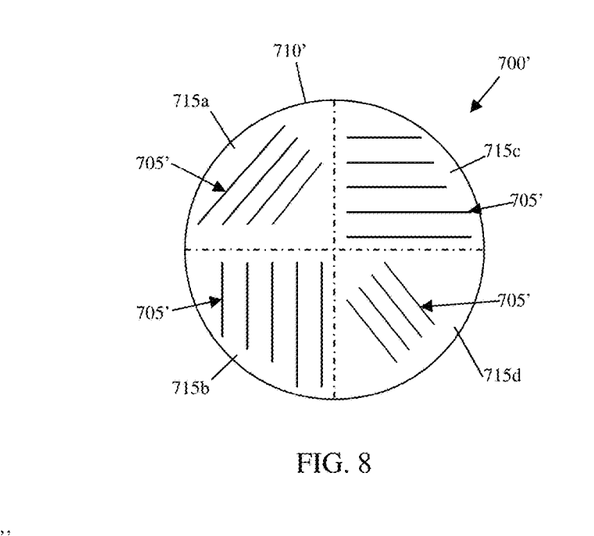

A single surface of the tissue expander (e.g., the bottom exterior surface) may have different ridges oriented in different directions to prevent movement in many different directions. For example, as shown in FIG. 8, a backside outer surface of the shell 710' of the tissue expander 700' may be divided into four areas 715a-d, and each area may have a plurality of ridges 705' that extend in a direction that is unique to that area. The differently aligned treads 705' in the different areas 715a-d contribute to a multi-vector tissue expander stability to different directional forces within the patient body. Numbers of areas other than four may be used within the scope of the invention. The areas need not be of the same size as one another, and need not be the same shape as one another.

Figure 9:
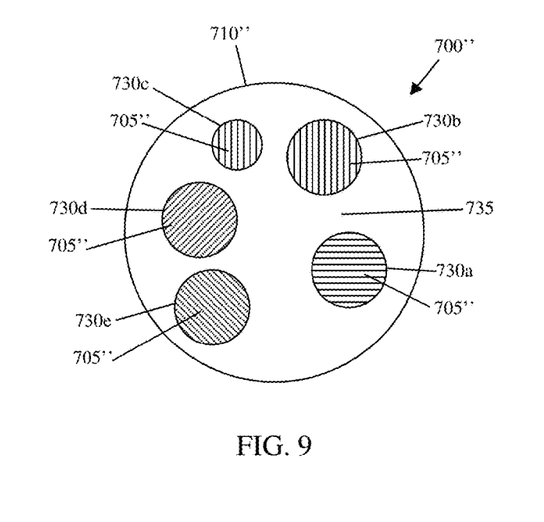

FIG. 8 shows the tread 705' covering substantial the entire backside outer surface of the shell. FIG. 9 shows an embodiment of a tissue expander 700'' in which less than the entire backside outer surface of the shell 710'' is provided with tread spots 730a-e. Each of the tread spots 730a-e may have plural treads 705'' aligned in a different direction than the other spots. The tread spots 730a-e may be added by adhesive, weld, or may be integrally molded with the exterior surface of the tissue expander. Untreaded areas 735 of the backside outer surface of the shell 710'' between the tread spots 730a-e also permit tissue to wedge between the tread spots 730a-e and thus further assist with stabilizing the implanted tissue expander 700'' inside the patient. Different spots may have different shapes (e.g., different diameters).

Figure 10:
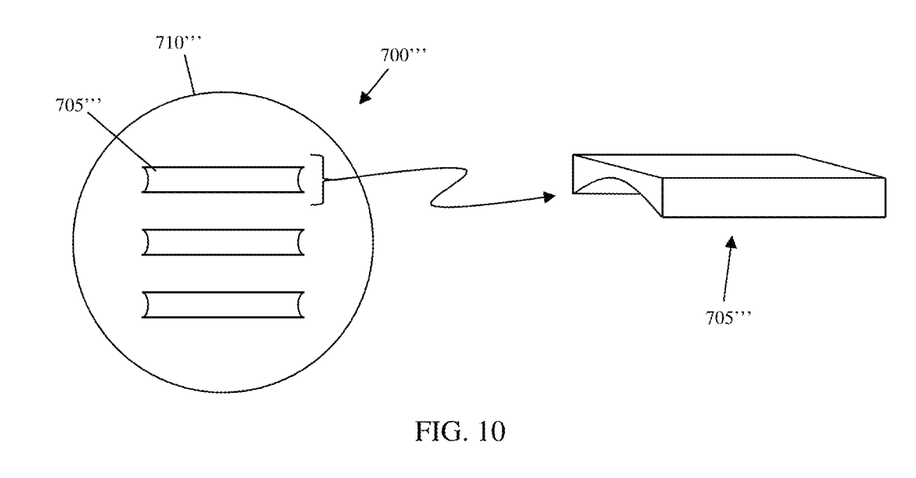
Figure 11:
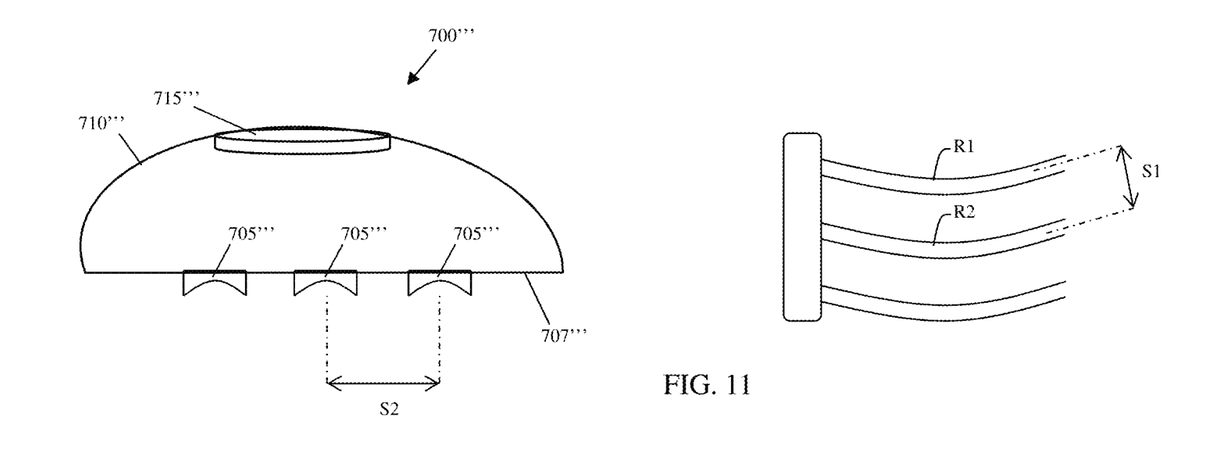

As shown in FIGS. 10 and 11, the tread 705''' may have a concave shape that is configured to fit against a rib bone in the patient in which the tissue expander 700''' is implanted. For example, the tissue expander 700''' may have three or so such treads 705''' on a backside outer surface of the shell that is configured to rest against the patient chest wall when the tissue expander 700''' is implanted in the patient. As shown in FIG. 11, the treads 705''' may be specifically placed on the tissue expander 700''' (e.g., by adhesive, weld, etc.) to match the spacing "S1" of the patient's ribs R1, R2. Specifically, the spacing "S1" of the ribs R1, R2 may be measured, and the tissue expander 700''' may be constructed by forming or attaching the treads 705''' on the backside outer surface of the shell such that the spacing "S2" between adjacent treads 705''' matches the measured spacing "S1" of the ribs R1, R2. The treads 705''' may be selected from a plurality of different size treads to closely match the size (e.g., diameter) of the particular patient ribs. Alternatively, the diameter of a rib R1 may be measured, and the tread 705''' that is associated with that rib may be formed (e.g., constructed) to match the measured diameter of the rib, e.g., such that the diameter of the concave surface of the tread 705''' is the same as the measured diameter of the rib. In this manner, different ones of the treads 705''' on a single tissue expander may have different diameters of their respective concave surfaces, based on the measured diameters of the individual ribs of the patient.

Any one or more of the various tread aspects described with respect to FIGS. 7-11 may be used with any type of tissue expander, including but not limited to any of the tissue expanders depicted in FIGS. 1-4. Any one or more of the various tread aspects described with respect to FIGS. 7-11 may be used alone or with the colorant described with respect to FIGS. 5 and 6 and/or the locator described with respect to FIGS. 12-14.

Locator

Figure 12:
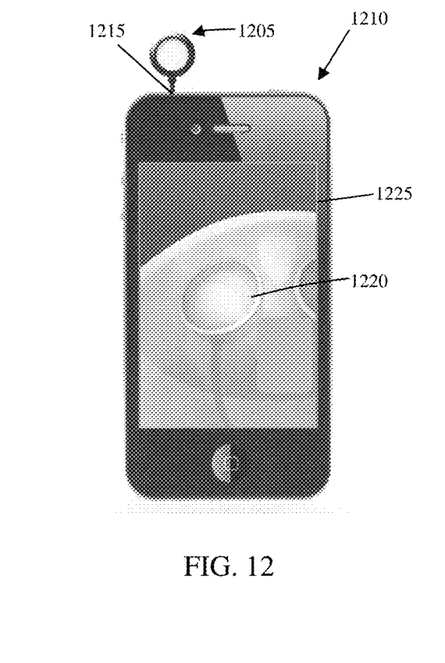
FIGS. 12-14 show aspects of a tissue expander locator in accordance with aspects of the invention.
Figure 13:
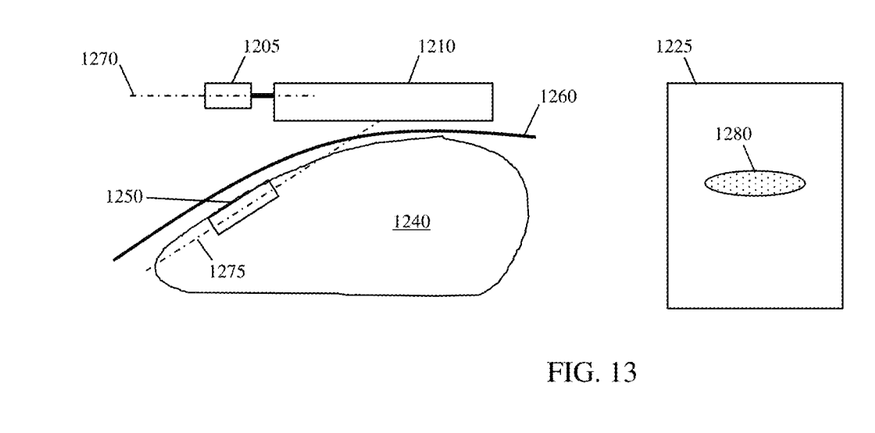
Figure 14:
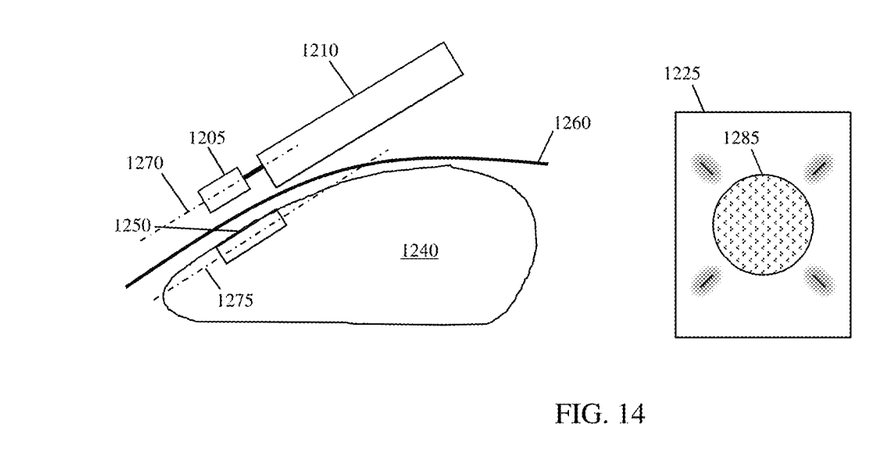

FIGS. 12-14 show aspects of a tissue expander locator in accordance with aspects of the invention. A problem with current tissue expanders is that, when the tissue expander is implanted and covered by the patient skin, the tissue expander is not visible to the medical professional and is at risk of having its shell punctured by a needle when the medical professional is attempting to insert that needle through the access port, e.g., for insufflating (e.g., injecting saline into) the implanted tissue expander. Missing the access port with the needle can puncture the tissue expander and deflate the tissue expander, which requires the patient to undergo another surgery to replace the damaged tissue expander. Implementations of the invention provide a technical solution to this problem by providing a computer-based locator that is configured to locate an access port of a tissue expander that is under the skin of a patient (i.e., implanted under the skin, not visible to the naked eye), and display a location of the access port on a visual display of a computing device, thereby guiding the medical professional to the access port and minimizing the risk of inadvertently puncturing the tissue expander. This solution helps the medical professional insert the insufflation needle into the access port in a direction that is perpendicular to the plane of the access port.

In embodiments, a portable or a hand held computing device is provided with hardware and software that is structured and arranged to locate a port of a tissue expander that is under the skin of a patient (i.e., implanted under the skin, not visible to the naked eye), and display a location of the port on a visual display of the computing device. The hand held computing device may be a smartphone or the like. In a particular smartphone embodiment depicted in FIG. 12, an electromagnetic detecting device 1205 is attached to the smartphone 1210, e.g., via the input/output port 1215 of the smartphone 1210. Software running on the smartphone 1210 interprets signals from the electromagnetic detecting device 1205 and produces a visual display 1220 of the detected port on the display 1225 of the smart phone 1210. The electromagnetic detecting device 1205 is configured to detect the metallic access (fill) port of the tissue expander and produce signals that are used to create the display 1220 based on such detection.

As shown in FIGS. 13 and 14, the detection and resulting visual display are sensitive to roll, pitch, and yaw about three orthogonal axes. In this manner, the roll/pitch/yaw orientation of the smartphone 1210 with the installed electromagnetic detecting device 1205 can be changed by the user (e.g., medical professional) by moving the smartphone 1210, and the visual display of the port will change accordingly.

For example, FIGS. 13 and 14 depict a tissue expander 1240 including an access port 1250 implanted in a patient (e.g., under skin 1260). The tissue expander 1240 and access port 1250 may be the same as or similar to a tissue expander and access port already described herein with respect to FIGS. 1-4. A smartphone 1210 having the detecting device 1205 is on an opposite side of the skin 1260 from the tissue expander 1240. As shown in FIG. 13, when the smartphone 1210 and the attached detecting device 1205 are positioned such that a first plane 1270 of the detecting device is not substantially parallel to a second plane 1275 of the port 1250, the display 1225 of the smart phone 1210 displays a first shape 1280 that indicates incorrect alignment. As shown in FIG. 14, when the smartphone 1210 and the attached detecting device 1205 are moved into a position such that a first plane 1270 of the detecting device 1205 is substantially parallel to a second plane 1275 of the port 1250, the display 1225 of the smartphone 1210 displays a second shape 1285 that indicates correct alignment. As used herein, substantially parallel means exactly parallel with a tolerance of plus or minus a few degrees (e.g., 5 degrees) of rotation in any one or more of the roll, pitch, and yaw directions.

The software may be configured to provide an audible and/or visual indication of when the electromagnetic detecting device 1205 is in a predefined "correct" location and orientation relative to the port 1250. For example, the indication may be a change in color (red for wrong, green for correct), a change in size and or shape (bigger circle when in the correct location and orientation), or cross hairs may appear when in the correct location and orientation, etc. In particular embodiments, the first shape 1280 is a different shape than the second shape 1285. For example, the first shape 1280 may be elliptical based on the detected angular difference between the first plane 1270 and the second plane 1275, and the second shape 1285 may be circular. In particular embodiments, the first shape 1280 is a different color than the second shape 1285. For example, the first shape 1280 may be red and the second shape 1285 may be green to provide a visual indication of the correct alignment of the detecting device 1205 relative to the unseen port 1250. In further embodiments, the smartphone 1210 or the detecting device 1205 are provided with a light that is activated to project a pattern on the patient skin when the correct alignment is achieved. In this manner, implementations of the invention may be used to (1) locate the tissue expander port under the skin, and (2) determine a spatial orientation of the injection plane of the tissue expander port, so that the medical professional can insert a needle through the skin and into the tissue expander port at an angle that is perpendicular to the injection plane of the tissue expander port.

Any one or more of the various locator aspects described with respect to FIGS. 12-14 may be used with any type of tissue expander, including but not limited to any of the tissue expanders depicted in FIGS. 1-4. Any one or more of the various locator aspects described with respect to FIGS. 12-14 may be used alone or with the colorant described with respect to FIGS. 5 and 6 and/or the tread described with respect to FIGS. 7-11.

Additional aspects of the invention include manufacturing a tissue expander with one or more of the improvements described herein. Even further aspects of the invention include providing instructions for using a tissue expander having one or more of the improvements described herein, e.g., instructions for how to implant and/or insufflate the tissue expander as described herein. The instructions may be at least one of printed and video.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A system, comprising:
 a computing device with a visual display screen;
 a detector connected to the computing device that is configured to detect a port of a tissue expander that is implanted under skin of a patient;
 software running on the computing device that receives signals from the detector and causes the visual display screen to show a visual representation of a location of the detected port of the tissue expander.

2. The system of claim 1, wherein the detector and software change the display based on changing at least one of the location and orientation of the detector relative to the port.

3. The system of claim 1, wherein the detector and software change the display based on at least one of translating, rolling, pitching, and yawing the detector relative to the port.

4. The system of claim 1, wherein the detector and software change the display to show a visual indicator when the detector is located and oriented in a correct position relative to the port.

5. The system of claim 1, wherein the computing device is a smartphone.

6. The system of claim 5, wherein the software is an app running on the smartphone.

7. The system of claim 1, wherein the computing device is a hand held computing device.

8. The system of claim 7, wherein the visual display screen is integral with the hand held computing device.

9. The system of claim 1, wherein the detector comprises an electromagnetic detecting device.

10. The system of claim 9, wherein the electromagnetic detecting device detects a metallic portion of the port.

11. The system of claim 9, wherein the electromagnetic detecting device detects a metallic portion of the port that is not visible to the naked eye of a user holding the computer device.

12. The system of claim 9, wherein the electromagnetic detecting device detects changes in roll, pitch, and yaw about three orthogonal axes.

13. The system of claim 1, wherein the system is configured such that:

the visual display screen displays a first shape in response to the computer device and the detector being positioned such that a first plane of the detector is not substantially parallel to a second plane of the port; and
 the visual display screen displays a second shape, different than the first shape, in response to the computer device and the detector being positioned such that the first plane of the detector is substantially parallel to the second plane of the port.

14. The system of claim 13, wherein the first shape indicates incorrect alignment and the second shape indicates correct alignment.

15. The system of claim 13, wherein the first shape has a different color than the second shape.

16. The system of claim 13, wherein the first shape has at least one of a different size and a different shape than the second shape.

17. The system of claim 13, wherein cross hairs are displayed with the second shape and are not displayed with the first shape.

18. The system of claim 1, wherein the computer device is configured to provide at least one of an audible and a visual indication of when the detector is in a predefined correct location and orientation relative to the port.

19. A system, comprising:
 a computing device with a visual display screen;
 a detector connected to the computing device that is configured to detect a port of a tissue expander that is implanted under skin of a patient;
 software running on the computing device that receives signals from the detector and causes the visual display screen to show a visual representation of a location of the detected port of the tissue expander,
 wherein the computer device is configured to activate a light that projects a pattern on the skin of the patient in response to correct alignment being achieved.

20. A system, comprising:
 a computing device comprising a visual display screen and a detector that detects an access port of a tissue expander that is implanted under skin of a patient; and
 software running on the computing device that receives signals from the detector and causes the visual display screen to show a visual representation of a location of the detected access port of the tissue expander,
 wherein the software changes the display based on changing at least one of the location and orientation of the detector relative to the access port.

* * * * *